United States Patent [19]

Reynolds

[11] 4,007,226

[45] Feb. 8, 1977

[54] NITRILE HYDROGENATION PROCESS

[75] Inventor: Jefferson W. Reynolds, Kingsport, Tenn.

[73] Assignee: Eastman Kodak Company, Rochester, N.Y.

[22] Filed: Jan. 31, 1973

[21] Appl. No.: 328,211

Related U.S. Application Data

[62] Division of Ser. No. 59,368, July 29, 1970, Pat. No. 3,728,284.

[52] U.S. Cl. ............................ 260/563 D; 252/459; 260/251 R; 260/309.2; 260/482 R; 260/561 R; 260/534 R; 260/570.8 R; 260/570.9; 260/583 K

[51] Int. Cl.$^2$ .................. C07C 85/10; C07C 87/14

[58] Field of Search ............... 252/459; 260/563 D, 260/583 K

[56] References Cited

UNITED STATES PATENTS

| | | | |
|---|---|---|---|
| 3,255,248 | 6/1966 | Suessenguth et al. | 260/563 D |
| 3,728,284 | 4/1973 | Reynolds | 252/459 |

*Primary Examiner*—Carl F. Dees
*Attorney, Agent, or Firm*—Edward R. Weber; Daniel B. Reece, III

[57] ABSTRACT

A hydrogenation catalyst of high activity, good crush strength and strong resistance to disintegration when employed in a fixed-bed hydrogenation process comprising a hydrogen-reduced mixture of sodium silicate and cobalt oxide in a weight ratio of sodium silicate:cobalt oxide of about 1:1 to 1:9.

6 Claims, No Drawings

NITRILE HYDROGENATION PROCESS

This is a division, of application Ser. No. 59,368 filed July 29, 1970, U.S. Pat. No. 3,728,284.

This invention relates to a novel hydrogenation catalyst composition useful particularly in the hydrogenation of nitriles to amines.

Amines, particularly primary and secondary amines, have found extensive utility in chemistry and the literature is full of reference to methods for preparing the same. One of the common methods of preparing amines is by the hydrogenation of nitriles in the presence of a fixed bed of solid catalyst. A wide variety of hydrogenation catalysts have been employed in this reaction but none have been entirely free from criticism. A serious fault of many fixed-bed solid hydrogenation catalysts is their inadequate crush or mechanical strength. For instance, commercially available fixed-bed cobalt or nickel catalysts are guickly softened under nitrile hydrogenation conditions to the point of disintegration. Disintegration is, of course, undesirable since it results in plugging of the reactor bed with consequent loss of efficiency. Other criticisms of conventional nitrile hydrogenation catalysts have been cost, inadequate catalyst life and complicated preparation procedures.

One of the objects of the invention is to prepare a hydrogenation catalyst of high activity, improved physical strength such as good crushing strength and a strong resistance to disintegration when employed in a fixed-bed hydrogenation process.

Another object of the invention is to provide a catalyst composition that is easily prepared from readily available materials.

Yet another object of the invention is to prepare a catalyst composition having a long active life in the preparation of amines by the hydrogenation of nitriles and which catalyst does not require sintering or fusion in its preparation.

A further object of the invention is to provide a process for the production of high yields of amines by the hydrogenation of nitriles.

These and other objects of the invention are obtained by a catalyst composition comprising a hydrogen-reduced mixture of sodium silicate and cobalt oxide in a weight ratio of sodium silicate:cobalt oxide of about 1:1 to 1:9, preferably about 1:1.5 to 1:5.

The catalyst composition of the invention may be easily prepared by mixing an aqueous sodium silicate solution and an oxide of cobalt (calculated as CoO) in a weight ratio of dry sodium silicate to cobalt oxide of about 1:1 to 1:9, preferably about 1:1.5 to 1:5, forming the resulting mixture in macrosize particles, drying the macrosize particles and subjecting the macrosize particles to hydrogen reduction. Any cobalt oxide may be used and cobalt oxide in a hydrate form such as cobalt oxide hydrate is preferred. Preferred sodium silicates are those wherein the mole ratio of $Na_2O:SiO_2$ is about 2:1 to 1:5.

Formation of the mixture of sodium silicate and cobalt oxide into macrosize particles may be by suitable methods such as extrusion, pelleting, tableting and the like. The preferred method is by extrusion since the paste-like mixture of the composition may be extruded without any complicated intermediate treatments such as washing or drying. The macrosize particles generally have diameters of about 1/32 to ¼ inch and lengths of about 1/32 inch up to about ½ inch or more.

After the macrosize particles have been properly dried, they are subjected to hydrogen reduction in accordance with methods well known in the art. The reduction temperature generally employed is about 300° to 500° C. Complete reduction is not necessary to obtain a catalyst having the desired activity and physical strength and, in fact as will be shown in the working examples below, incomplete reduction appears to provide a finished catalyst not only equal in activity to a completely reduced catalyst but of greater durability. It should be understood that preparation of the catalyst of the invention does not require treatments such as sintering, fusing, etc., usually necessary to activate the catalyst.

Although the catalysts of the invention are useful in hydrogenation reactions generally, they are particularly useful in the hydrogenation of nitriles. Any monomeric nitrile having the general formula $R(C \equiv N)_n$ is catalytically hydrogenated by hydrogen gas to primary and secondary amines in the presence of the catalyst of the invention. In the above general formula, n is any whole number from 1 to 4 inclusive, preferably 1 to 2 and R may be any hydrocarbon radical substituted or unsubstituted, preferably of 1 to 18 carbon atoms. R, therefore, may be aliphatic, alicyclic, aromatic, aliphatic-aromatic, aromatic-aliphatic, or heterocyclic structures including, by way of example, hydrocarbon radicals and substituted hydrocarbon radicals containing substituent hydroxyl, keto, carboxyl, halogen, aldehyde, ether, amine, amide, imide, nitro, nitroso and the like groups in any combination. Furthermore, it is to be understood that the presence of such hydrogen-reducible groups as ethylenic or acetylenic unsaturation in the nitrile does not make such nitriles inoperative for the purposes of the invention.

Illustrative of typical nitriles which can be hydrogenated in the presence of the catalyst of the invention to provide the primary and secondary amines include, but are not limited to, acetonitrile, propionitrile, butyronitrile, isobutyronitrile, capronitrile, caprylonitrile, myristonitrile, lauronitrile, stearonitrile, acrylonitrile, crotononitrile, hexenonitrile, 3-octenenitrile, oleonitrile, tridecanenitrile, 2-butynenitrile, 2,4-pentadienenitrile, 1-cyclopentanecarbonitrile, 1-cyclohexanecarbonitrile, 1,3-cyclopentadiene-5-carbonitrile, succinonitrile, adiponitrile, sebaconitrile, 1,4-dicyanobutene-2, 1,4-dicyanobutene-1, 4,4-dimethyl-2-heptene-1,7-dinitrile, dodecanedinitrile, 1,3.5-pentanetricarbonitrile, 1,4-cyclohexanedicarbonitrile, 1,4-cyclohexanetetracarbonitrile, 1,1,3-cyclohexanetripropionitrile, benzonitrile, 2-naphthonitrile, isophthalonitrile, terephthalonitrile, 1-phenylpropionitrile, trimesonitrile, α-ethyl-β-oxocapronitrile, isonipicotonitrile, 5-pyrimidinecarbonitrile, 2-cyano-3-heptenoic acid, α-cyanoacetamide, p-cyanobenzaldehyde, α-cyanoglutarimide, α-hydroxyisobutyronitrile, 2-benzimidazoleacetonitrile, phenylacetonitrile, valeronitrile, ethyl cyanoacetate, phenoxybutyronitrile, cyanoacetamide, malononitrile, 3-butenenitrile, cyanoacetic acid, undecanenitrile, β-isopropoxypropionitrile, β-methoxy-propionitrile, toluonitrile, anisonitrile, fluorene-9,9-bis(propionitrile) and the like.

The amount of catalyst employed in the fixed-bed nitrile hydrogenations of the invention is, in all instances, a catalytic amount.

The fixed-bed hydrogenation of the nitrile is generally conducted at a temperature of about 50° to 135° C. and at a pressure of at least 250 psi., usually up to about 3000 psi. or possibly more. It is to be understood, of course, that the optional temperature and pressure employed depends somewhat upon the nitrile and the particular catalyst employed. In any case, a suitable temperature and pressure will be chosen which promote an acceptable reaction rate.

Advantageously, ammonia is introduced to the hydrogenation in order to suppress side reactions. When employed, the ammonia is present in the mole ratio of ammonia to nitrile of about 2:1 to 30:1

An inert organic solvent or diluent is not necessary but may be employed, if desired, and may be advantageous particularly where the reaction is highly exothermic. Substantially any organic solvent or diluent which is inactive both with respect to reaction with the $Na_2O$:-$SiC_2$-CoO catalyst and the nitrile will be satisfactory. Suitable inert organic solvents or diluents include, by way of example, methanol, ethanol, 2-propanol, methyl acetate, benzene, toluene, cyclohexane, heptane, petroleum ether, dioxane, diethyl ether, and the like. The amount of such inert solvent or diluent can vary widely, but should be used in an amount which would not greatly increase recovery costs or interfere with isolation of the desired primary and secondary amine products. The process of the invention may be carried out as a batch process or as a continuous or semi-continuous process, as desired.

The following examples are to further illustrate preparation of the catalysts of the invention.

EXAMPLE I - 20% Sodium Silicate-Cobalt (Calculated as CoO)

A paste is prepared from 149.5 g. of sodium silicate solution (38.8% by weight aqueous solution of 1 $Na_2O$:3.25 $SiO_2$) and 300 g. of cobalt oxide hydrate (61% cobalt) and extruded into ⅛ inch extrusions. The extrusions are dried at room temperature and then slowly dried further in a tube furnace. The dried material is reduced in hydrogen at 350° C. to provide a catalyst having a bulk density of 28 lbs./cu. ft. and a crushing strength of 2 pounds.

EXAMPLE II - 40% Sodium Silicate-Cobalt (Calculated as CoO)

The procedure of Example I is repeated using twice as much sodium silicate solution with the cobalt oxide hydrate. The resulting hydrogen-reduced catalyst has a bulk density of 72 lbs./cu. ft. and a crushing strength of 10 pounds.

EXAMPLE III - 20% Sodium Silicate-Cobalt (Green) and 20% Sodium Silicate-Cobalt (Black) (Calculated as CoO)

The procedure of Example I is repeated except that the reduction with hydrogen is conducted at 300° C. Black extrudates form at the top of the bed which is the first part to be contacted with hydrogen and green extrudates (partially reduced) are formed downstream. The average bulk density of the reduced catalyst is 30 lbs./cu. ft. The crushing strength of the green extrudate is found to be twice that of the black extrudate, 4 pounds vs. 2 pounds.

EXAMPLE IV

A paste which contains 30% sodium silicate on a dry basis is prepared from cobalt oxide hydrate (61% cobalt) from Shepherd Chemical Company and an aqueous sodium silicate solution (40% by weight of 1 mole $Na_2O$:2.54 moles $SiO_2$) from Moreland Chemical Company, formed into ⅛ inch extrusions and dried at room temperature. The extrudates, cut to ¼ to ⅜ inch, are slowly dried further in a tube furnace in nitrogen. Hydrogen is gradually introduced into the nitrogen stream to the material, and it is finally reduced 2 hours in hydrogen at 450° C. The bulk density of the resulting black catalyst is 30 lb./cu. ft., and its crushing strength is 4 pounds.

The following examples are included to demonstrate the activity and durability of the catalysts in nitrile hydrogenation.

EXAMPLES V – IX

Various nitriles are hydrogenated in the presence of a fixed bed of the catalyst of Example I to the corresponding saturated diamines by the following general procedure:

The autoclave is charged with the nitrile dissolved in inert solvent and the catalyst basket containing the catalyst is connected to the autoclave cover. The autoclave is purged with nitrogen, sealed, charged with ammonia in four of the five runs and placed in the magnetic stirrer barricaded in a cubicle. The magnetic stirrer is started and the contents heated to reaction temperature. The system is pressurized by hydrogen to the desired pressure and maintained at this pressure by hydrogen additions during the reaction period. At the completion of the reaction, the stirrer and heater are turned off, the autoclave cooled to 50° C., vented and the reaction product and catalyst removed. The product is analyzed by gas chromatography and the catalyst examined. The hydrogenation conditions and results are summarized in Table 1 below. Portions of the catalyst of Example I are used to hydrogenate fluorene-9,9-bis(3-propionitrile) (FBN), 1,4-cyclohexanedicarbonitrile (CDN) and 4,4-dimethyl-2-heptene-1,7-dinitrile (DHN). The conditions and results of these hydrogenations are also reported in Table 1.

TABLE 1

| Ex. | Catalyst[a] | Nitrile[b] | Auto-Clave | Time, Hr.[c] | Temp., °C | Pressure Psi. | Moles $NH_3$; Moles Nitrile | Nitrile[d] Gms. | Solvent[e] | Activity[f] % | Catalyst Condition |
|---|---|---|---|---|---|---|---|---|---|---|---|
| V | 20% Sodium Silicate-Cobalt | FBN | Gal. | 48 | 125 | 1000 | 10:1 | 570 (2) | 2-Propanol-Toluene | 64 | Good |
| VI | 20% Sodium Silicate-Cobalt | FBN | 1.5 l. | 48 | 125 | 600–1000 | None | 200 | Toluene | 53 | Good |
| VII | 20% Sodium Silicate-Cobalt | FBN | 1.5 l. | 301 | 125 | 1000–1500 | 10.1 | 1000 (5) | Toluene | >95 | Good |

TABLE 1-continued

| Ex. | Catalyst[a] | Nitrile[b] | Auto-Clave | Time, Hr.[c] | Temp., °C | Pressure Psi. | Moles NH₃; Moles Nitrile | Nitrile[d] Gms. | Solvent[e] | Activity[f] % | Catalyst Condition |
|---|---|---|---|---|---|---|---|---|---|---|---|
| VIII | 20% Sodium Silicate-Cobalt | CDN | Gal. | 205 | 125 | 1000 | 10:1 | 1140 (4) | 2-Propanol-Toluene | ~100 | Good |
| IX | 20% Sodium Silicate-Cobalt | DHN | 1 l. | 4 | 125 | 600 | 10:1 | 30 | 2-Propanol | 93 | Good |

[a] Used 15 g. of catalyst
[b] FBN = Fluorene-9,9-bis(3-propionitrile)
CDN = 1,4-cyclohexanedicarbonitrile
DHN = 4,4-dimethyl-2-heptene-1,7-dinitrile
[c] Run length was normally 4, 24 or 48 hrs.
[d] Total amount of nitrile is given; more than one charge is indicated in parentheses
[e] 1 l. autoclave - 150 ml., 1.5 l. autoclave - 500 ml. and 1 gal autoclave - 1500 ml. per charge; ratio of 2-propanol:toluene was 1:4
[f] Activity is determined from percent diamine + ½ percent aminonitrile in the product As can be seen from the data in Table 1, the catalyst of the invention is active for the hydrogenation of fluorene-9,9-bis(3-propionitrile), 1,4-cyclohexanedicarbonitrile and 4,4-dimethyl-2-heptene-1,7-dinitrile and that the condition of the catalyst on completion of the hydrogenations is good. The olefin bond in the latter nitrile is also hydrogenated.

EXAMPLES X – XI

Fluorene-9,9-bis(3-propionitrile) (FBN) is hydrogenated as in Examples V – IX in the presence of fixed beds of both the black and green catalysts of Example III. The hydrogenation conditions employed and the results obtained are reported in Table 2.

TABLE 2

| Ex. | Catalyst[a] | Nitrile[b] | Auto-Clave | Time, Hr.[c] | Temp., °C | Pressure Psi. | Moles NH₃; Moles Nitrile | Nitrile[d] Gms. | Solvent[e] | Activity[f] % | Catalyst Condition |
|---|---|---|---|---|---|---|---|---|---|---|---|
| X | 20 Sodium Silicate-Cobalt (Green) | FBN | 1.5 l. | 96 | 125 | 1500 | 10:1 | 400 (2) | Toluene | ~100 | Good |
| XI | 20 Sodium Silicate-Cobalt (Black) | FBN | Gal. | 96 | 125 | 1500 | 10:1 | 570 (2) | Toluene | ~100 | Fair to Good |

Footnotes a – f (See Table 1)

The data of Table 2 shows that both catalysts exhibit high activity and the green catalyst, that is, the partially reduced catalyst is perhaps more durable. The green catalyst was not expected to be active.

EXAMPLE XII

Fluorene-9,9-bis(3-propionitrile) (FBN) is hydrogenated as in Examples V – IX in the presence of a fixed bed of the catalyst of Example II.

EXAMPLE XIII

A 15-g. portion of the catalyst of Example IV in a wire basket is tested in the hydrogenation of 100 g. of DHN dissolved in 400 ml. of 2-propanol using a 1.5-l. autoclave equipped with a magnetic stirrer capable of being turned at 1000 rpm. Ammonia is added to the autoclave to give a molar ratio of 10 ammonia:1 nitrile. The hydrogenation conditions employed and the results of the hydrogenation of Examples XII and XIII are shown in the following Table 3.

TABLE 3

| Ex. | Catalyst[a] | Nitrile[b] | Auto-Clave | Time, Hr.[c] | Temp., °C | Pressure Psi. | Moles NH₃; Moles Nitrile | Nitrile[d] Gms. | Solvent[e] | Activity[f] % | Catalyst Condition |
|---|---|---|---|---|---|---|---|---|---|---|---|
| XII | 40% Sodium Silicate-Cobalt | FBN | 1.5 l. | 48 | 125 | 1500 | 10:1 | 200 | Toluene | 50 | Good |
| XIII | 30% Sodium Silicate-Cobalt | DHN | 1.5 l. | 48 | 100 | 600 | 10:1 | 100 | 2-Propanol | 70 | Good |

Footnotes a – f (See Table 1)

This data of Table 3 shows that the 30 and 40% sodium silicate-cobalt catalyst of the invention are active and durable nitrile hydrogenation catalysts.

EXAMPLES XIV – XVIII

Fluorene-9,9-bis(3-propionitrile) (FBN), and 4,4-dimethyl-2-heptene-1,7-dinitrile (DHN) are hydrogenated as in Examples V – IX in the presence of a fixed bed of various commercial catalysts. The hydrogenation conditions employed and the results of the hydrogenation are shown in the following Table 4.

TABLE 4

| Ex. | Catalyst[a] | Nitrile[b] | Auto-Clave | Time, Hr.[c] | Temp., °C | Pressure Psi. | Moles $NH_3$: Moles Nitrile | Nitrile[d] Gms. | Solvent[e] | Activity[f] % | Catalyst Condition |
|---|---|---|---|---|---|---|---|---|---|---|---|
| XIV | Girdler G-67RS | FBN | Gal. | 48 | 125 | 750 | 10:1 | 285 | 2-Propanol-Toluene | 85 | Disintegrated |
| XV | Girdler G-67HS | FBN | 1.5 l. | 24 | 125 | 1000 | 10:1 | 200 | 2-Propanol-Toluene | 86 | Disintegrated |
| XVI | Girdler G-69RS | DHN | 1.5 l. | 48 | 100 | 600 | 10:1 | 100 | 2-Propanol | 89 | Disintegrated |
| XVII | Harshaw Ni-3210 | FBN | 1.5 l. | 48 | 100 | 1000 | 10:1 | 200 | 2-Propanol-Toluene | ~100 | Disintegrated |
| XVIII | American Cyanamid Aero 295 | DHN | 1.5 l. | 144 | 100 | 600 | 5:1 | 200 | 2-Propanol | 82 | Disintegrated |

Footnotes a - f (See Table 1)

The data of Table 4 shows the disintegration of the various commerical catalysts and by comparison with the previous data emphasizes one of the advantages of the catalyst of this invention.

The invention has been described in considerable detail with particular reference to certain preferred embodiments thereof, but it will be understood that variations and modifications can be effected within the spirit and scope of the invention.

I claim:

1. A process for the preparation of primary and secondary amines which comprises subjecting a monomeric nitrile of the formula $R(C\equiv N)_n$ wherein R is a hydrocarbon radical of 1 to 18 carbons and $n$ is a number of 1 to 4, to hydrogenation with a gas consisting essentially of hydrogen at a temperature of about 50° to 135° C. and a pressure of about 250 to 3000 psi in the presence of a hydrogenation catalyst comprising non-sintered macrosize particles of a hydrogen-reduced mixture of sodium silicate and an oxide of cobalt wherein the weight ratio of sodium silicate to the oxide of cobalt, figured as CoO, is from about 1:1 to about 1:9.

2. The process of claim 1 wherein ammonia is employed in the hydrogenation in a mole ratio of ammonia to nitrile of about 2:1 to 30:1.

3. The process of claim 2 wherein the catalyst composition has a weight ratio of sodium silicate to cobalt oxide of 1:1.5 to 1.5.

4. The process of claim 2 wherein the nitrile is fluorene-9,9-bis(3-propionitrile).

5. The process of claim 2 wherein the nitrile is 1,4-cyclohexanedicarbonitrile.

6. The process of claim 2 wherein the nitrile is 4,4-dimethyl-2-heptene-1,7-dinitrile.

* * * * *